(12) United States Patent
Barnhizer

(10) Patent No.: US 8,413,800 B2
(45) Date of Patent: Apr. 9, 2013

(54) FLAT PACKAGING OF PETRI DISHES FOR PROLONGED PRESERVATION AND METHOD OF PRODUCING THE SAME

(76) Inventor: Bret T. Barnhizer, Hubbard, OH (US)

( * ) Notice: Subject to any disclaimer, the term of this patent is extended or adjusted under 35 U.S.C. 154(b) by 0 days.

(21) Appl. No.: 13/449,857

(22) Filed: Apr. 18, 2012

(65) Prior Publication Data

US 2012/0261277 A1    Oct. 18, 2012

Related U.S. Application Data

(60) Provisional application No. 61/476,738, filed on Apr. 18, 2011.

(51) Int. Cl.
*B65D 81/28* (2006.01)
*B65B 31/04* (2006.01)
*C12M 3/00* (2006.01)

(52) U.S. Cl. .............. 206/213.1; 53/434; 435/305.4; 435/309.4; 435/801; 435/810

(58) Field of Classification Search .......... 206/213.1, 206/524.8; 53/426, 434; 435/305.2–305.4, 435/309.1–309.4, 801, 810
See application file for complete search history.

(56) References Cited

U.S. PATENT DOCUMENTS

| | | | | |
|---|---|---|---|---|
| 2,874,091 | A * | 2/1959 | Fisk | 435/305.2 |
| 3,751,341 | A * | 8/1973 | Seitz et al. | 435/309.4 |
| 4,295,563 | A * | 10/1981 | Becker et al. | 206/213.1 |
| 4,458,019 | A * | 7/1984 | Chrisope | 435/801 |
| 4,588,561 | A * | 5/1986 | Aswell et al. | 435/810 |
| 4,709,819 | A | 12/1987 | Lattuada et al. | |
| 4,988,302 | A * | 1/1991 | Smith et al. | 435/305.4 |
| 5,034,331 | A * | 7/1991 | Brewer | 435/305.4 |
| 5,234,105 | A * | 8/1993 | Sato et al. | 206/213.1 |
| 6,059,457 | A * | 5/2000 | Sprehe et al. | 206/524.8 |
| 6,670,174 | B1 * | 12/2003 | Smith et al. | 435/305.4 |

* cited by examiner

*Primary Examiner* — Bryon Gehman
(74) *Attorney, Agent, or Firm* — Acker Wood IP Law, LLC; Gwen R. Acker Wood

(57) ABSTRACT

The present invention provides an improved flat package of petri dishes and method of producing the same for prolonging shelf life and preservation of sterility of the petri dishes. The flat package is comprised of an optically clear, high-barrier, moisture-, gas- and microbial-resistant pouch. A plurality of petri dishes located adjacent one another are placed in an interior cavity of the pouch, after which the pouch is vacuum-packed, optionally flushed with an inert gas and then heat sealed. The placement and immobilization of the petri dishes in the pouch allow for prolonged shelf life and preservation of sterility, greatly reduced breakage rates, and enhanced visibility of the petri dishes by a user.

19 Claims, 4 Drawing Sheets

FLAT PACKAGING OF PETRI DISHES FOR PROLONGED PRESERVATION AND METHOD OF PRODUCING THE SAME

CROSS REFERENCE TO RELATED APPLICATIONS

The present application claims priority to U.S. Provisional Application No. 61/476,738, filed Apr. 18, 2011, which is incorporated by reference herein.

FIELD OF THE INVENTION

The present invention relates to packaging of medical supplies and, in particular, to an improved packaging of petri dishes which enhances visibility, reduces immobility and prolongs shelf life and sterility of the packaged petri dishes therein.

BACKGROUND OF THE INVENTION

The typical petri dish used by clinicians, scientists and others to culture microorganisms or cells is a shallow polystyrene plastic lidded dish of varying dimensions. Petri dishes usually are sold in packages of twenty dishes, in which each dish is stacked directly on top of one another and surrounded by a plastic sleeve. An illustration of a prior art package of petri dishes contained in a plastic sleeve is shown in FIG. 1.

Current packaging of petri dishes as described above poses several disadvantages. First, if one or more of the petri dishes become contaminated or are defective in some way, visibility of such contamination or defect either is not possible, due to packages that are opaque or light impervious, and thus do not allow inspection by the user prior to use, or at best limited to only certain portions of each dish due to the stacking of the dishes directly on top of one another. Second, petri dishes in a plastic sleeve have a fair amount of mobility in the sleeve, thus allowing for slippage, resulting in an average breakage rate to one or more of the petri dishes of about 20%. Third, average shelf-life of a typical plastic sleeve of petri dishes is only about three months.

There exists a need, therefore, to provide an improved package for storing and shipping petri dishes which overcomes the disadvantages encountered with currently available packaged petri dishes.

SUMMARY OF THE INVENTION

The present invention fulfills this need by providing an improved flat package ("flat-pack") of petri dishes and method of producing the same for prolonged shelf life and preservation of the petri dishes.

In one aspect, the present invention provides a flat package containing a plurality of petri dishes for prolonged shelf life and preservation thereof, comprised of an optically clear, high-barrier, moisture-, gas- and microbial-resistant pouch. The pouch has an interior cavity which contains a plurality of petri dishes immobilized therein, in which each of the plurality of petri dishes is located adjacent one another. The clarity of the pouch and the placement and immobilization of the petri dishes therein allow for prolonged shelf life and preservation of sterility of the petri dishes, greatly reduced breakage rates, and enhanced visibility of each of the petri dishes which allows for easy inspection of the petri dishes for contamination and/or breakage by the user.

In another aspect, the present invention provides a method of producing a flat package containing a plurality of petri dishes for prolonged shelf life and preservation thereof. The method comprises obtaining a sterile, optically clear, high-barrier, moisture-, gas- and microbial-resistant pouch, inserting a plurality of sterile petri dishes within an interior cavity of the pouch, in which each of the petri dishes are located adjacent to another petri dish, applying a vacuum to the interior cavity of the pouch to evacuate atmospheric air from the pouch, optionally flushing the interior cavity of the pouch with an inert gas, and heat sealing the pouch.

In one embodiment, the flat package has an easy open means, such as a zip-lock.

The pouch and each of the plurality of petri dishes in accordance with the present invention are handled aseptically in an aseptic environment to ensure sterility.

The pouch may be comprised of a visibly clear, transparent plastic material such as, without limitation, polypropylene, oriented polypropylene (OPP), polyethylene terephthalate (PET) or combinations thereof.

The number of petri dishes contained in the flat package can range from about ten to about twenty petri dishes. In one embodiment, the plurality of petri dishes is aligned in one plane of the pouch.

The flat package in accordance with the present invention maintains sterility and provides a shelf life to the petri dishes contained therein of at least twelve months.

BRIEF DESCRIPTION OF THE DRAWINGS

A complete understanding of the present invention will be obtained from the following description taken in connection with the accompanying drawing figures, in which.

DETAILED DESCRIPTION OF THE INVENTION

Figure 1:
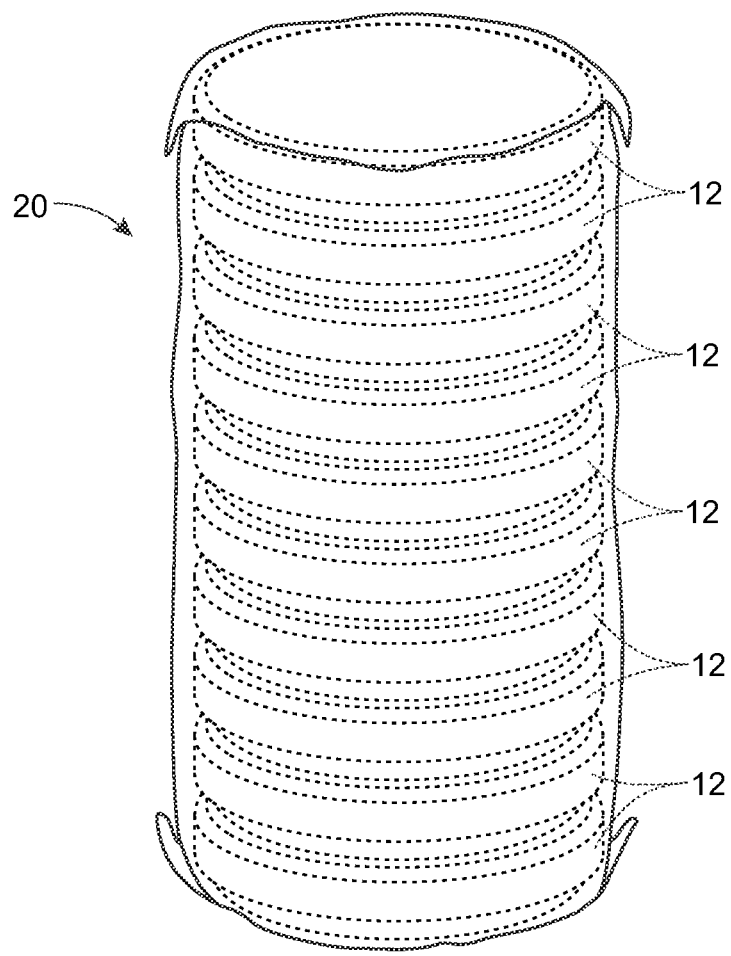
FIG. 1 is an illustration of a prior art package of stacked petri dishes surrounded in a cylindrical plastic sleeve.

As used herein, the terms "petri dish," "dish" and "monoplate" are meant to be interchangeable.

As used herein, the term "flat package" and "flat-pack" are meant to be interchangeable.

As used herein, the term "shelf life" is meant to refer to the length of time a petri dish may be stored without becoming unsuitable for sale or use.

A complete understanding of the present invention will be obtained from the following detailed description taken in connection with the accompanying drawing figures, wherein like reference characters identify like parts throughout.

Figure 2:
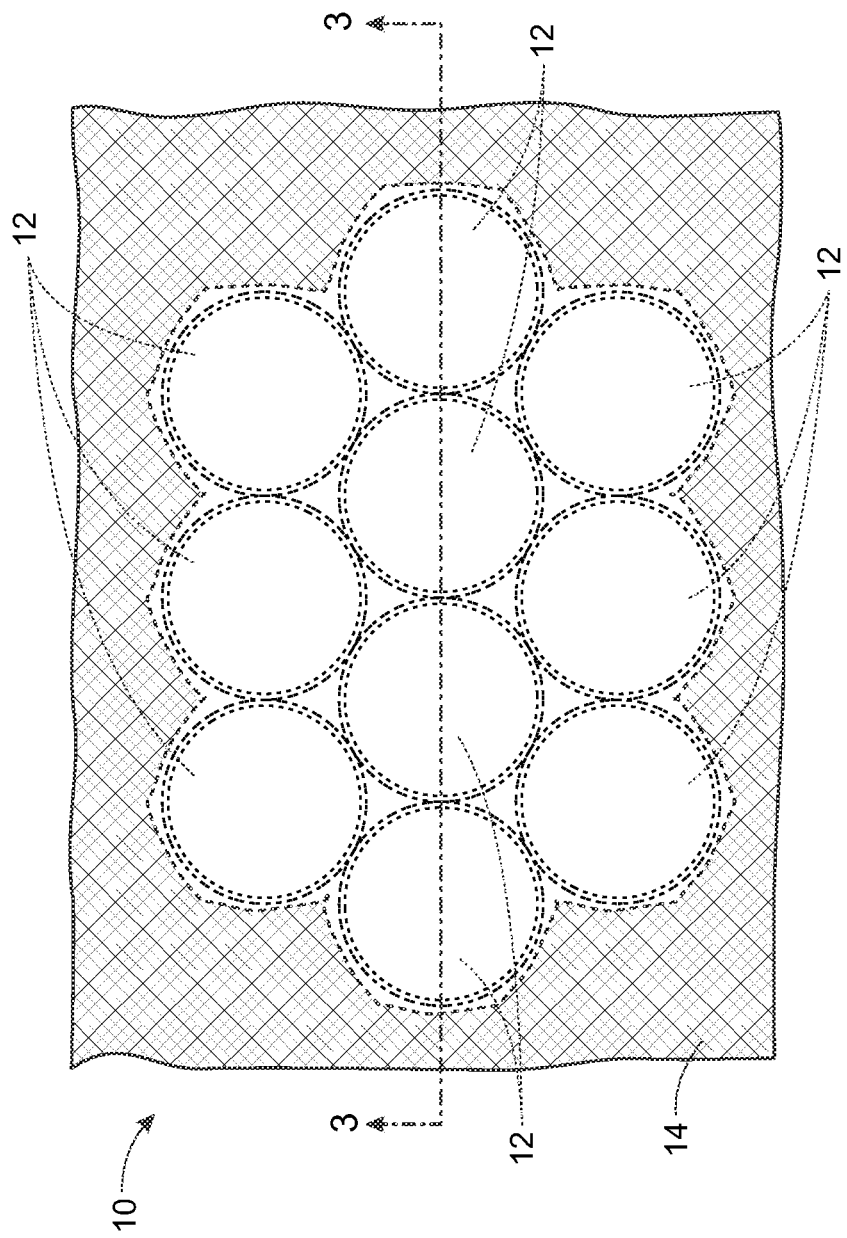
FIG. 2 is a top view of a plurality of petri dishes packaged in a flat package in accordance with the present invention.
Figure 3:
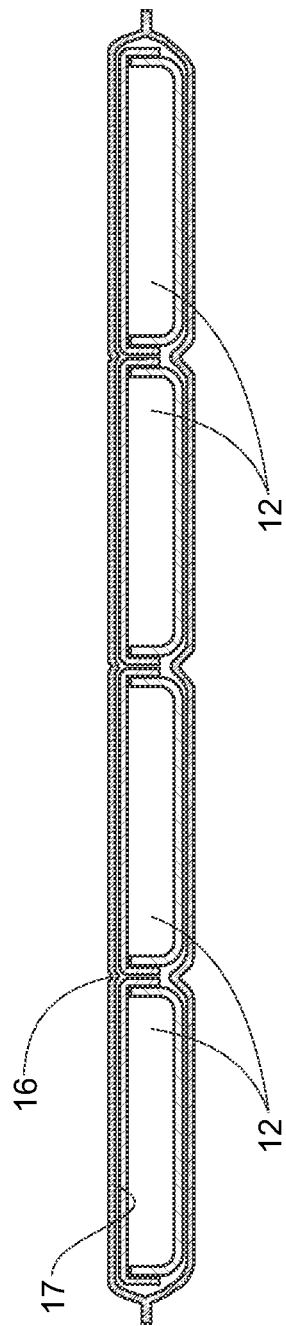
FIG. 3 is a cross-sectional view taken at line 3-3 of FIG. 2 showing each petri dish located adjacent to another petri dish in accordance with the present invention.
Figure 4:
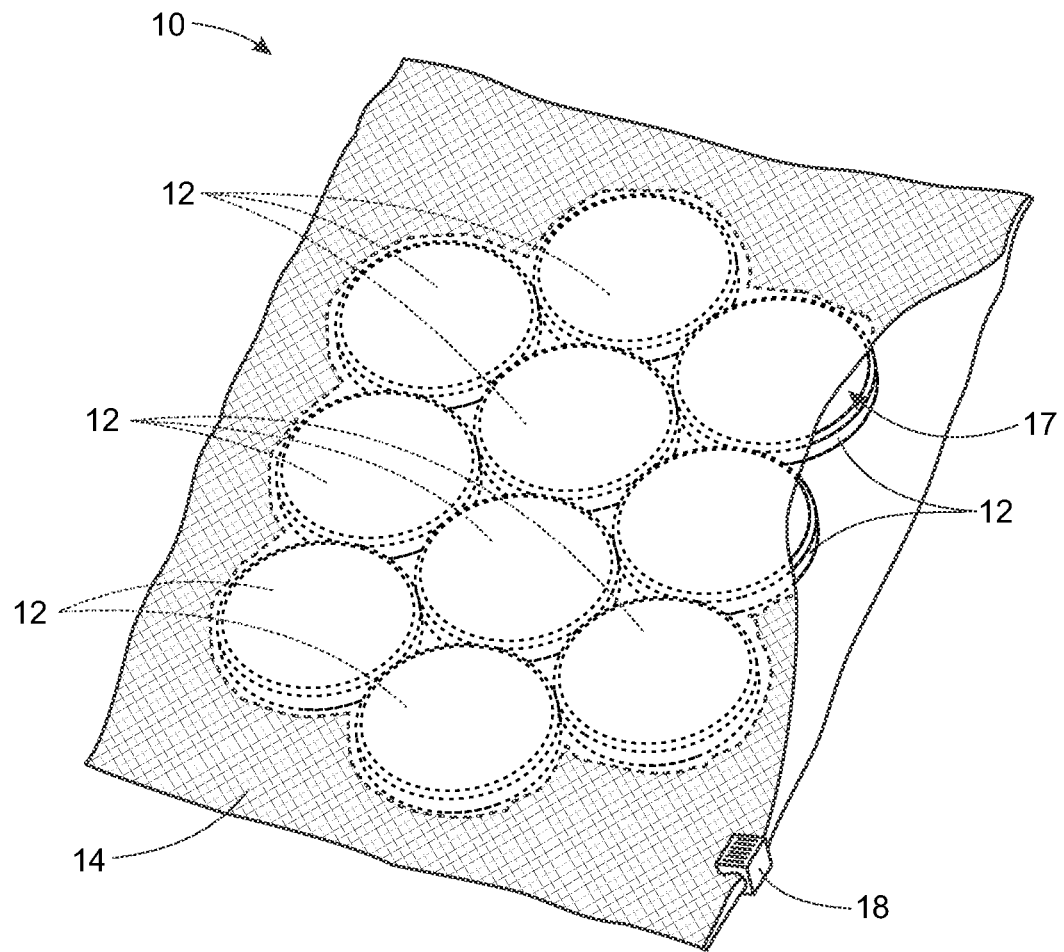
FIG. 4 is a perspective view of the flat package having therein a plurality of petri dishes in accordance with the present invention.

Referring now to the drawings, FIG. 2 shows a flat-pack 10 of a plurality of petri dishes 12 in accordance with the invention. The flat pack 10 comprises a pouch 14 in which a plurality of petri dishes 12 is contained and immobilized therein. As shown in FIGS. 3 and 4, the pouch 14 has an interior cavity 17 with each of the plurality of petri dishes 12 located therein. Each of the plurality of petri dishes 12 is located adjacent to another petri dish 12 with very little separation 16 there between (best shown in FIG. 3).

As shown in FIG. 4, the pouch 14 may include an easy open means 18. The easy open means 18 may include, without limitation, a peelable means, a zipper means, a zip-lock means, or any other suitable easy open means used by those skilled in the art. In an embodiment, the easy open means is a zip-lock 18.

The present invention also provides a method of producing a flat-pack of petri dishes for prolonged preservation of petri dishes. The method comprises the steps of providing a sterile, optically clear, high-barrier, moisture-, gas- and microbial-resistant pouch, inserting a plurality of sterile petri dishes within an interior cavity of the pouch, in which each of the petri dishes are located adjacent to another petri dish, applying a vacuum to the pouch to evacuate atmospheric air from the interior cavity of the pouch, optionally flushing the interior cavity of the pouch with an inert gas, and then heat sealing the pouch.

Vacuum packing, or vacuum packaging, is a method of packaging that removes air from a package prior to sealing. It typically is used to remove oxygen from a container to extend the shelf life of the contents therein and to limit the growth of aerobic bacteria and fungi. Vacuum packing in accordance with the invention may be accomplished using any suitable vacuum device, such as, without limitation, a vacuum chamber, which is capable of reducing air pressure within the interior cavity of a pouch to about 0.5 mbars. After evacuation, the pouch may be flushed with an inert gas, such as nitrogen gas. After flushing with the inert gas, the pouch is heat sealed. Suitable heat sealing processes may include, without limitation, pneumatic heat sealing methods.

The pouch in accordance with the invention may be fabricated from a visibly clear plastic material such as, without limitation, polypropylene, oriented polypropylene (OPP), polyethylene terephthalate (PET) or combinations thereof, so long as it is optically clear, forms a high-barrier to the environment and is moisture-, gas- and microbial-resistant.

The optical clarity of the pouch, the placement of the petri dishes adjacent to one another, and immobilization of the petri dishes therein due to vacuum packing and, optionally, nitrogen flushing, of the pouch in accordance with the present invention, allow for enhanced visibility of each of the petri dishes, greatly reduced breakage rates, and prolonged shelf life and preservation of sterility of the petri dishes. In contrast to prior art packaging of petri dishes, any defect or contamination to one or more of the petri dishes in the flat-pack of the invention from microorganisms, chemicals, ultraviolet light or any other contaminant can easily be detected by the user.

Thus, the present invention provides the following significant advantages and improvements over prior art packaging of petri dishes: (1) ability to easily visualize and inspect each of the petri dishes for defect or contamination, in contrast to prior art stacked packages of petri dishes, where visibility of dishes that are between the top and the bottom of the stack is very limited (see FIG. 1); (2) increased cushioning of the petri dishes due to the placement of each petri dish side by side, rather than directly on top of one another; and (3) greatly reduced mobility of the petri dishes in the flat-pack, due to vacuum packing the flat-pack subsequent to inserting the petri dishes, in contrast to prior art packages of petri dishes which are not vacuum-packed and thus not immobile. Immobility of the petri dishes provided by the present invention substantially eliminates breakage of the petri dishes in the flat-pack.

The flat-pack of petri dishes in accordance with the invention allows for a surprisingly long shelf life of the petri dishes, i.e., an average of at least twelve months or longer. This is in contrast to prior art packaged petri dishes which have an average shelf-life of about three months.

It will be appreciated that the number of petri dishes the pouch of the flat package of the present invention may accommodate will depend on the size of the pouch as well as the size of each petri dish contained therein. Typical petri dishes have dimensions (diameter×height) of 35 mm×10 mm, 60 mm×15 mm, 100 mm×20 mm or 150 mm×25 mm. In one embodiment, the pouch of the flat package may accommodate about ten to about twenty petri dishes having dimensions of 35 mm×10 mm, 60 mm×15 mm, or 100 mm×20 mm. In another embodiment, the pouch of the flat package may accommodate about five to about ten petri dishes having a dimension of 150 mm×25 mm.

The petri dishes in the flat-pack of the present invention may be placed adjacent one another aligned in one plane of the pouch. Alternatively, the petri dishes may be doubled up to form two rows of adjacent petri dishes.

The shape of the pouch in accordance with the invention may include shapes such as, without limitation, circular, rectangular, elliptical, square, or any other shape to accommodate the number of petri dishes therein.

EXAMPLES

The improved flat package for prolonged shelf life and preservation of petri dishes of the present invention is further described in the following non-limiting example, which is intended to be illustrative only of the superior properties of the invention when compared to prior art packaging of petri dishes, as numerous modifications and variations therein will be apparent to those skilled in the art.

Example 1

Comparison of Flat-Packs of Petri Dishes to Prior Art Packaged Petri Dishes

Various vendors provide Tryptic Soy Agar (TSA) monoplates. The product provided by NanoLogix, Inc. (NNLX) however, was differentiated by its unique packaging. Referred to as a "flat-pack," it includes ten monoplates arranged in a sturdy, honey-combed configuration in a single layer, i.e., plates are not stacked atop each other. In addition, the polymer wrapper pouch is sealed with a vacuum, further enhancing the sturdiness of the packaging. Other vendors typically stack monoplates atop one another in a plastic package, or sleeve, in quantities of ten or more, resulting in a cylindrical configuration. These cylindrical packages are not vacuum sealed. As a result, heavy condensation can occur within the monoplates. Further, due to the lack of vacuum packing, petri dishes in a cylindrical package are not immobilized. Because typical petri dishes are fabricated from polystyrene plastic, they then are susceptible to damage if their shipping box is roughly handled. Thus, there is a significant breakage rate of the dishes during the course of shipping.

A shelf life test for TSA monoplates (NNLX, Lot No. 0006513) produced, packaged, and shipped by NNLX was conducted by Battelle Memorial Institute. After delivery, each monoplate in the flat-packs was visually inspected for damage or contamination, which was easily performed due to the transparency of the packaging and the placement of the monoplates in the flat-packs. It was noted that none of the NNLX TSA monoplates in the flat-packs was damaged or exhibited condensation.

The shelf life test was conducted over a twelve month period and involved comparing NNLX TSA monoplates packaged in flat-packs with TSA monoplates packaged in conventional cylindrical plastic sleeves, using purified *Bacillus anthracis* Ames spores in serial dilutions on each of the monoplates. Colonies were enumerated after 18 to 24 hours of incubation at 37±2° C. The quantitative values of bacterial growth on the monoplates from the third party vendor were compared to bacterial growth on the NNLX TSA monoplates.

The results showed that average colony forming units per milliliter (CFU/ml) of spores plated on the third party vendor TSA monoplates were $1.07 \times 10^9$ CFU/ml. The NNLX TSA monoplates averaged $9.60 \times 10^8$ CFU/ml. The coefficient of variance of 7.47% was within the acceptable criteria for enumerated colonies.

These results were surprising, as the shelf-life of TSA monoplates from the third party vendor typically is no more than about three months, yet the NNLX TSA monoplates supported comparable colony growth after 12 months. After about three months, TSA monoplates from the third party vendor typically show dryness or desiccation of the media, exhibited by a thinner agar layer. In contrast, the NNLX TSA monoplates from flat-packs maintained the initial agar thickness over the course of the 12 months. Further, the enumeration results suggest that the nutrients within the media used by NanoLogix (BD Soybean-Casein) were sufficiently viable, i.e., did not dry out or desiccate in the petri dish packaged in a flat-pack after 12 months, which allowed for promotion of similar colony growth to that of the third party vendor's TSA having a significantly shorter shelf life of 3 months.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A flat package containing a plurality of petri dishes with nutrient media contained therein for prolonged shelf life and preservation thereof, comprising: an optically clear, high-barrier, moisture, gas and microbial-resistant pouch, said pouch having an interior cavity and containing a plurality of sterile nutrient media-containing petri dishes immobilized therein, each of said plurality of petri dishes located adjacent one another aligned substantially in a coplanar arrangement cushioned within the interior cavity of the pouch, wherein the pouch is heat-sealed after having air be evacuated from the interior cavity of the pouch, and wherein the clarity of the pouch, the immobility, alignment and cushioning of the petri dishes therein, and the evacuation of air allow for prolonged shelf life and preservation of sterility of the petri dishes and the nutrient media contained therein, substantially no breakage of the petri dishes, and enhanced visibility of each of the petri dishes by a user.

2. The flat package according to claim 1, wherein the plurality of petri dishes are aligned in one plane of the pouch.

3. The flat package according to claim 1, wherein the pouch is comprised of a visibly clear plastic material selected from the group consisting of polypropylene, oriented polypropylene (OPP), polyethylene terephthalate (PET) and combinations thereof.

4. The flat package according to claim 1, wherein the interior cavity of the pouch is flushed with an inert gas after the evacuation of air therefrom.

5. The flat package according to claim 4, wherein the inert gas is nitrogen gas.

6. The flat package according to claim 1, wherein the pouch is heat sealed.

7. The flat package according to claim 1, wherein the pouch has a zip-lock for easy opening and closing.

8. The flat package according to claim 1, wherein the pouch and the plurality of petri dishes are handled aseptically in an aseptic environment.

9. The flat package according to claim 1, wherein the plurality of petri dishes consists of about ten to about twenty petri dishes.

10. The flat package according to claim 1, wherein the shape of the pouch is selected from the group consisting of circular, rectangular, elliptical and square.

11. The flat package according to claim 1, wherein the plurality of petri dishes and the nutrient media contained therein have a shelf life and remain sterile for at least twelve months.

12. A method of producing a flat package containing a plurality of petri dishes with nutrient media contained therein for prolonged shelf life and preservation thereof, comprising:
   obtaining an optically clear, high-barrier, moisture-, gas- and microbial-resistant pouch, said pouch having an interior cavity;
   inserting the plurality of petri dishes within the interior cavity of the pouch, each of said plurality of petri dishes located adjacent one another and aligned substantially in a coplanar arrangement, said plurality of petri dishes being immobilized within the interior cavity of the pouch;
   evacuating air from the interior cavity of the pouch and the plurality of petri dishes therein;
   flushing the pouch with atmospheric gas or an inert gas; and
   heat sealing the pouch, wherein the clarity of and cushioning by the pouch, the immobilized placement and substantially coplanar arrangement of the petri dishes therein, and the evacuation of air allow for prolonged shelf life and preservation of sterility of the petri dishes and the nutrient media contained therein, substantially no breakage of the petri dishes, and enhanced visibility of each of the petri dishes by a user.

13. The method according to claim 12, wherein the plurality of petri dishes are aligned in one plane of the pouch.

14. The method according to claim 12, wherein the pouch is comprised of a visibly clear plastic material selected from the group consisting of polypropylene, oriented polypropylene (OPP), polyethylene terephthalate (PET) and combinations thereof.

15. The method according to claim 12, wherein the inert gas is nitrogen gas.

16. The method according to claim 12, wherein the sealed pouch has a zip-lock for easy opening and closing.

17. The method according to claim 12, wherein the pouch and the plurality of petri dishes are handled aseptically in an aseptic environment.

18. The method according to claim 12, wherein the plurality of petri dishes consists of about ten to about twenty petri dishes.

19. The method according to claim 12, wherein the plurality of petri dishes and the nutrient media contained therein have a shelf life and remain sterile for at least twelve months.

* * * * *